United States Patent
Horino et al.

Patent Number: 6,156,324

Date of Patent: *Dec. 5, 2000

[54] COMPOSITIONS FOR COSMETICS AND COSMETICS

[75] Inventors: Masaakira Horino, Kanagawa; Yukio Hasegawa, Kasukabe, both of Japan

[73] Assignee: Miyoshi Kasei, Inc., Saitama, Japan

[*] Notice: This patent is subject to a terminal disclaimer.

[21] Appl. No.: 08/859,320

[22] Filed: May 20, 1997

[51] Int. Cl.[7] .............................. A61K 7/00; A61K 7/42; C09C 1/02; C09D 1/00

[52] U.S. Cl. .................. 424/401; 106/286.4; 106/286.6; 106/287.11; 106/493; 106/465; 424/59; 424/60; 424/63; 424/64; 424/400

[58] Field of Search ................................ 424/59, 60, 400, 424/401, 63, 64; 106/286.4, 286.6, 465, 490, 287.12, 493

[56] References Cited

U.S. PATENT DOCUMENTS

| | | | |
|---|---|---|---|
| 5,306,486 | 4/1994 | McCook et al. | 424/59 |
| 5,744,126 | 4/1998 | Horino et al. | 424/59 |

FOREIGN PATENT DOCUMENTS

| | | |
|---|---|---|
| 0 443 086 | 6/1991 | European Pat. Off. . |
| 0 668 071 | 8/1995 | European Pat. Off. . |
| 47-42502 | 10/1972 | Japan . |
| 58-62106 | 4/1983 | Japan . |
| 61-229809 | 10/1986 | Japan . |
| 62-228006 | 10/1987 | Japan . |
| 2-194065 | 7/1990 | Japan . |
| 2-196028 | 8/1990 | Japan . |
| 2-196029 | 8/1990 | Japan . |
| 3-279323 | 12/1991 | Japan . |
| 5-156174 | 6/1993 | Japan . |
| 6-59397 | 8/1994 | Japan . |
| 7-23294 | 3/1995 | Japan . |
| WO 9304666 | 3/1993 | WIPO . |
| WO 96/28136 | 9/1996 | WIPO . |

OTHER PUBLICATIONS

WPI Abstract Accession No. 97–337025 & JP 09–136815 (see Abstract).

WPI Abstract Accession No. 94–269334 & JP 06–199634 (see Abstract).

WPI Abstract Accession No. 91–276704 & JP 03–181411 (see Abstract).

*Primary Examiner*—Shelley A. Dodson
*Attorney, Agent, or Firm*—Armstrong, Westerman, Hattori, McLeland & Naughton

[57] ABSTRACT

Cosmetic compositions and cosmetics which have good dispersibility, high UV protection effect that lasts for a long period and high stability with suppressed optical activity and catalytic activity. The cosmetic contains 10.5 weight % of a composition comprising fine-grain titanium oxide (mean particle size 0.9 μm) treated with 5% methylhydrogenpolysiloxane, zinc oxide (mean particle size 2.5 μm) treated in the same manner and talc (mean particle size 4 μm) treated in the same manner.

14 Claims, No Drawings

COMPOSITIONS FOR COSMETICS AND COSMETICS

The present invention relates to cosmetic compositions and the cosmetics containing them, more precisely to cosmetic compositions which have good dispersibility and high UV protection effect, suppress the optical activity and catalytic activity of UV protection material, do not show changes upon aging and show high stability, and the cosmetics containing said cosmetic compositions.

It is well known that UV-light has many malignant influences on the human skin. UV-light can be classified into the long wave length region of 400–320 nm wave length (UV-A wave), middle wave length region of 320–290 nm (UV-B wave), and the range below 290 nm (UV-C wave). UV-C wave is absorbed in the ozone layer and therefore mostly cannot reach the earth. UV-B wave which reaches the earth produces red spots and water blisters, and furthermore promotes melanine-formation when an optical amount higher than a threshold amount is irradiated to the human skin. Comparing UV-A wave with UV-B wave, the former produces fewer red spots than the latter and makes the skin black, without producing the red spots substantially. Furthermore, UV-A wave has strong penetration ability into the skin, promotes bridge-making of the collagen, i.e., the skin protein, lowers the elasticity and water-preserving ability of collagen and induces wrinkles formation, causes spots and freckles formation and induces skin aging. It is known that UV-A wave induces skin cancer, because it increases the amount of peroxidized lipid in skin structure.

In order to protect the skin against UV-related diseases, cosmetics which are blended with UV absorption materials have been developed up to now and brought to commercial market. For such cosmetics, synthetic UV absorbers such as benzophenones, aminobenzoic acids, cinnamic acid esters, benzotriazoles, salicylic acids, dibenzoylmethanes and inorganic pigment, such as fine-grain titanium oxide, zinc oxide and iron oxide are employed.

However, there are problems in that synthetic UV absorption materials cannot exhibit their full effects, because of their low dispersibility and solubility, when their addition to cosmetic basic materials increases. Especially although benzotriazoles and dibenzoylmethanes are known effective UV absorptive materials against UV-A wave, they are solid at room temperature and have low solubility, and in oil gels and emulsions the presence of a trace amount of metallic ion precipitates pale yellow crystals with the lapse of time or soft particulate yellow-orange masses sediments due to complex formation. Furthermore, they have some associated disadvantages in that these phenomena affect the external appearance and impair the commercial value.

In order to cut off a wide range of UV, UV scattering materials are employed. As UV scattering materials, ultra fine-grain inorganic oxides such as titanium oxide, zinc oxide, zirconium oxide, cerium oxide, iron oxide, etc., are used, and they are used also in common sunburn cosmetics. Although they cut off a wide range of UV and are useful for the safety of skin, they also have many associated disadvantages which the following JP Patent Kokai publication describes. Accordingly, they are not always satisfactory.

In JP Patent Kokoku publication JP-B-47-42502, sunburn cosmetics blended with titanium oxide which can cut off UV-B wave and has mean particle size 30–40 μm are disclosed. However, titanium oxide is a substance which cuts off UV-B wave and cannot cut off effectively UV-A wave, without being used in high blend concentration. High blend concentration of titanium oxide results in high shielding potency, however leaves whitish spots after application. This impairs external appearance of the cosmetics and furthermore, the dispersibility into cosmetic basic material feel, and stability are not satisfactory.

In JP Patent Kokai publication JP-A-58-62106, cosmetics blended with hydrophobicated ultra fine-grain titanium oxide which can cut off UV-B wave and has mean particle size 10–30 μm are disclosed. However, similarly to the cosmetics in JP Patent Kokoku publication JP-B-47-42502, UV-A wave cannot be cut off without using a high concentration. Due to high blend concentration whitish spots remain after application, a powder-like appearance remains and the spreading capacity on the skin and adherence are not good, accordingly the product is not satisfactory.

In JP Patent Kokai publication, JP-A-61-229809 cosmetics blended with amorphous titanium oxide which cut off UV-B wave are disclosed. However, without a high blend concentration UV-A wave cannot be cut off. High concentration blend lowers SPF (Sun Protection Factor) values due to aggregation of particles and leaves whitish spots after application, and the spreading capacity on the skin and adherence to the skin are insufficient.

In JP Patent Kokoku publication JP-B-7-23294, cosmetics blended with ultra fine-grain zinc oxide are applied. Compared with ultra fine-grain titanium oxide, its UV shielding potency is $1/3$–$1/4$ of titanium oxide. For goods which require high SPF value, high concentration blend is necessary and the spreading on the skin and adherence to the skin are poor and insufficient. Cosmetics oils deteriorate due to the strong surface activity of ultra fine-grain zinc oxide and the resulting products are not satisfactory.

In JP Patent Kokai Publication JP-A-3-279723, sunburn compositions containing ultra fine-grain zinc oxide and ultra fine-grain titanium oxide are disclosed. Without high concentration (more than 13 weight %), high SPF value could not be obtained. With high concentration, shielding potency increases and whitish spots remain in the cosmetic layer, and with the lapse of time particles aggregate again to reduce SPF value and to cause deterioration of cosmetic oil and furthermore, to worsen its feel. It is possible that immediately after preparation of the above sunburn compositions high SPF values can be obtained, but because the above blended ultra fine-grain zinc oxide and the above blended ultra fine-grain titanium oxide exhibit surface activity, the aggregation after lapse of time (aggregation of one of the above ultra fine-grain zinc oxide and titanium oxide), deterioration and denaturation of blended cosmetic oils cannot be avoided.

In JP Patent Kokai publication JP-A-5-156174, pigment coating ZnO and $TiO_2$ are disclosed. However, because both kinds of particles stick on the surface of thin platelet powders, the powders behave as thin platelet powders. When the application surface on the skin to which the powders are applied is microscopically observed, gaps are observed between powders if high concentration blend is not used. Consequently, UV light transmits and high SPF value and high PFA values cannot be obtained. The PFA value can be measured with a SPF analyzer (Optometrics Co., SPF-290 analyzer). The higher the PFA value is, the harder UV light transmits.

The primary purpose of the present invention is to provide novel cosmetic compositions and cosmetics, and the secondary purpose of the present invention is to solve the problems due to the conventional preparation techniques and to provide novel highly stable cosmetic compositions and cosmetics which exhibit good dispersibility and high UV-shielding effect, where the effect lasts for a long period and wherein the optical activity and catalytic activity of UV-shielding materials are suppressed.

In these circumstances the present invention completed the present invention after long research work wherein fine-grain titanium oxide, zinc oxide and clay mineral are surface-treated with at least one silicone oil such as dimethylpolysiloxane, methylhydrogenpolysiloxane, etc., and the resulting compositions, wherein the following components are blended preferably in specific ratio, containing the above three types of basic materials treated with silicone exhibit better dispersibility and higher UV shielding effects than each single component of fine-grain titanium oxide and zinc oxide, due to their synergetic effects, and prevent the optical activity and the catalytic activity and show no aging change, and compositions with high stability and cosmetics containing them can be obtained.

According to the present invention, at least one of the above objects of the present invention can be achieved with the following cosmetic composition and cosmetics.

The first aspect of the invention is a cosmetic composition comprising fine-grain titanium oxide treated with silicone, zinc oxide treated with silicone and clay mineral treated with silicone.

In preferable cases, the relative properties (weight ratios) of the amount of the above fine-grain titanium oxide treated with silicone (expressed as a range) to the amount of the above zinc oxide treated with silicone and to the amount of the above clay mineral treated with silicone (expressed as a range) is 10–80:80–10:10–30, in more preferable cases, the composition ratio is 15–70:70–15:10–20, and in the most preferable cases the composition ratio is 45–65:30–10:10–20.

In other preferable cases, one or more of the above fine-grain titanium oxide treated with silicone, the above zinc oxide treated with silicone and the above clay mineral treated with silicone are aggregated secondarily.

In more preferable cases, the mean particle size of the above secondarily aggregated fine-grain titanium oxide is 0.5–3.0 $\mu$m, the mean particle size of the above-secondarily aggregated zinc oxide is 0.01–5.0 $\mu$m and the mean particle size of the above secondarily aggregated clay minerals is 1–25 $\mu$m.

In other preferable cases one or more of the above fine-grain titanium dioxide treated with silicone, the above zone-oxide treated with silicone and the above clay mineral treated with silicone is prepared by pulverizing and/or grinding one or more of the titanium oxide, zinc oxide and clay mineral with a jet stream and simultaneously adsorbing and combining silicone thereinto.

The second aspect of the invention is a cosmetic comprising the cosmetic composition described above.

In preferable cases, the above cosmetic composition is contained in the cosmetic in 0.5–50 weight % of the total weight of said cosmetic. In more preferable cases, the above cosmetic composition is contained in said cosmetic in 5–20 weight % of the total weight of said cosmetic.

Because the active points on the surface of each of the fine-grain titanium oxide, zinc oxide, zinc oxide and clay mineral are blocked with silicone, the optical activity and catalytic activity are suppressed and when they are used in cosmetics, these materials cause denaturation of other components in cosmetics only very seldom. Accordingly, they can prevent denaturation and odor of cosmetic oils and discoloring and fading of the tar pigment designated by law for use in cosmetics.

Furthermore, because fine-grain titanium oxide treated with silicone, zinc oxide treated with silicone and clay mineral treated with silicone have similar surface properties, the dispersibility of cosmetics is superior and reaggregation can be prevented.

The numerical range descriptions in the present invention are inclusive of not only both the upper and lower limits, but also all values between those limits.

EMBODIMENT OF INVENTION

Cosmetic Compositions

As surface treatment agent which is used to prepared each of the fine-grain titanium oxide treated with silicone, zinc oxide treated with silicone and clay mineral treated with silicone, silicone oils such as dimethylpolysiloxane, methylphenylpolysiloxane perfluorosilicone, polyether modified silicone having no reactive group can be used. However, methylhydrogenpolysiloxane with reactive group, trimethylsioxy silic acid, alkylpolysiloxane which has functional group(s) at one terminal end or on both sides of the silicone molecule, etc., can be used preferably.

Examples of the above alkylpolysiloxane are $\alpha$-dimethylpolysiloxysilazane, $\alpha$-monohydroxy-siloxane, $\alpha,\omega$-dihydroxypolymethylsiloxane, $\alpha$-monoalkoxypolydimethylsiloxane, $\alpha$-dialkoxypolydimethylsiloxane, $\alpha$-trialkoxypolydimethylsiloxane (e.g., $\alpha$-triethoxypolydimethylsiloxane, etc.) $\alpha,\omega$-dialkoxypolydimethyl-siloxane, $\alpha,\omega$-hexaalkoxypolydimethylsiloxane, dimethylpolysiloxychloride, diemthylpolysiloxybromide and dimethylpolysiloxyiodide.

As the surface treatment methods, a conventional mechanochemical method, a solvent method and a jet method which is described in JP Patent Kokoku Publication JP-B-6-59397 can be employed, especially the above jet method is suitable for dispersion and surface treatment of fine-grain powders. In the above jet method particles collide with each other in the high speed jet streams and the aggregated particles are dispersed in the states similar to primary original particles and simultaneously, because the active sites exposed in this process are covered with silicone, the above jet stream methods are suitable for surface treatment to obtain compositions according to the present invention and its constituent components.

To explain more precisely, in the jet stream methods in the above JP Patent Kokoku Publication JP-B-6-59397, the surface was treated mechano-chemically whereby shock force is imparted to the mixture of powder particles and surface-treated agents (silicone oil, etc.) with a jet stream, and surface-treated powder was obtained by adsorption or combination of the surface treatment agents on the surface. According to this method, a surface-treated powder can be obtained wherein the surface of the powder particles is uniform and the surface properties are improved.

In other words, in the above jet method, a jet stream is generated when highly pressurized air or stream is ejected through nozzles at high speed and the powder particles and surface treatment agents are introduced into the jet streams to pulverize and/or grind the above powder particles by mutual collision of particles and the above surface treatment agent is adsorbed and combined to he powder obtained by these grinding and collision methods.

In the above jet methods, the powders to be treated and surface treatment agents collide with each other in a high speed stream (several 10 m/s to several 100 m/s) and with this energy they are ground further and simultaneously surface treatment agents with high surface activity are adsorbed and combined uniformly and tightly. The surface treatment agents are adsorbed and combined in active sites of the fine-grain titanium oxide and fine-grain zinc oxide and the active sites on the resulting surface are covered. The treated powder surface is not contaminated with other materials and before starting of secondary aggregation the surface treatment agents are adsorbed and combined to the above surface. The powder particles before treatment with the above jet stream may be primary particles or secondary particles or mixtures thereof.

In the above jet method, without aggregating fine-grain particles obtained by pulverizing and/or grinding the above surface treatment agents are adsorbed or combined to every surface of the above particles. Accordingly, surface-treated powder without secondary aggregation can be obtained by the above jet method and secondary aggregated particles can be also obtained by condition changes (e.g., change of some parts of the production facilities).

For surface treatment procedures by the jet stream method, the jet stream grinding machine can be employed, i.e., a mixture of powder particles and surface treatment agents is placed into the jet stream grinding machine and shock force is imparted to the above mixtures with jet streams. The mixture is fluidized and stirred in the grinding machine and powders are surface-treated mechanochemically, and finally, surface treatment agents are adsorbed and combined with powders on the surface thereof.

Examples of the jet stream grinding machine are a fluid layer type, a spiral type and a jet atomizer type, and the fluid layer type is mostly appreciated because it can treat uniformly and effectively.

The cosmetic composition of the present invention contains, in preferable cases, the fine-grain titanium oxide treated with silicone, zinc oxide treated with silicone and clay mineral treated with silicone as the mixture thereof. The above mixture can be obtained by mixing together the fine-grain titanium oxide treated with silicone, zinc oxide treated with silicone and clay mineral treated with silicone obtained separately by the above surface treatment methods (preferably the jet method). In preferable cases titanium oxide, untreated zinc oxide and clay mineral can be processed by the above surface treatment methods (preferably the jet stream) for mixing and simultaneous silicone treatment.

The amount of the surface treatment agent is preferably 1–20 weight % of the total weight of silicone-treated material (fine-grain titanium oxide treated with silicone, zinc oxide treated with silicone or clay mineral treated with silicone). For example, the silicone weight is preferably 1–20 weight % of the total weight of the fine-grain titanium oxide treated with silicone. The silicone in either one of the above methods is chemically bound to the surface of UV-shielding materials having activated surfaces (fine-grain titanium oxide, zinc oxide and clay minerals). These coating states are supposed to be coated on the active center of UV-shielding materials (fine-grain titanium zinc oxide and clay minerals) by resin, gel or oil, etc., singly or by combination thereof.

In the case that the fine-grain titanium oxide surface-treated with silicone used for the composition according to the present invention such as dimethylpolysiloxane or hydrogenpolysiloxane, is composed of secondarily aggregated particles, the mean fine-grain particle size of the secondarily aggregated particles is preferably 0.5–3.0 $\mu$m (as measured by the laser method). The mean particle size of the primary particles of fine-grain titanium oxide which constitute the above secondarily aggregated particle is preferably 0.01–0.1 $\mu$m, more preferably 0.03–0.1 $\mu$m, most preferably 0.03–0.06 $\mu$m. By "secondary aggregated particles" is meant those particles in the aggregated states, wherein the particles in states similar to primary particles are flocculated through weak forces by silicone treatment.

The preparation methods of the fine-grain titanium oxide before silicone treatment may be any method for producing ultra fine-grain—fine-grain titanium oxide. For example, the methods described in JP Patent Kokai Publications JP-A-2-194065, 2-196028, and 2-196029 may be used to give the desired products for the present invention.

The ultra fine-grain titanium oxide having a single particle diameter limited to 10–50 nm UV reflects and scatters UV which has wavelength 290–320 nm, is biologically strongest and generates red spots and inflammation of the skin and has characteristics that visible light is transmitted through it. But, in the commercially available ultra fine-grain powders, strong aggregation takes place due to strong surface activity and a trace amount of adsorbed water. Accordingly, the particle size of optical substances which exhibit optical scattering plays the main role in scattering from the Reileigh region to Mie region and actually lowers the transparency. Accordingly, in cosmetics blended with ultra fine-grain titanium oxide, a blue-whitish color of the applied cosmetic layer becomes evident, particles which are dispersed by mechanical forces aggregate again with the lapse of time due to strong surface activity of the above ultra fine-grain titanium oxide and the SPF is lowered. Accordingly, the expected UV-protection effect cannot be achieved.

The particle size of the aggregation of the untreated ultra fine-grain titanium oxide is 1.2–5.0–5.0 $\mu$m (measurements with laser method) and as highly active spots remain, the adsorbed water is decomposed due to the irradiation of UV light to generate strong oxidizing OH and $OH_2$ free radicals. These radicals cause discoloration and fading of cosmetic tar pigment permitted for use by law and denaturation of cosmetic oils. On the other hand, for UV protection effect the untreated ultra fine-grain titanium oxide possesses 3–4 fold potential relative to that of fine-grain zinc oxide. For achieving high SPF value, the untreated ultra fine-grain titanium oxide is useful. If it is blended with cosmetics, a blue-whitish color results in the cosmetic layer and causes deterioration of the cosmetic effects, and problems remain in achievement of high SPF value. As the surface activity is high, these untreated materials again with he lapse of time and cause lowering of SPF value.

The ultra fine-grain and fine-grain titanium oxide is treated with silicone such as dimethylpolyoxysiloxane or hydrogenpolysiloxane and the active points on the surface of this powder are covered. Consequently, denaturation and changing of odor of the general cosmetic oil and discoloring and brown-changing of the cosmetic tar pigment permitted for se by law can be prevented, reaggregation of particle with lapse of time can be prevented, the mean particle size is small nd the dispersibility is improved, furthermore adherence to the skin is also improved and a long period durability of UV protection effect is assured.

In case that zinc oxide which is treated with silicone such as dimethyl-polysiloxane or hydrogenpolysiloxane is in the form of secondary aggregated particles, the mean particle size of such secondary aggregated particle (as measured by laser methods) is preferably 0.01 (more preferably 0.2 $\mu$m, most preferably 0.5 $\mu$m)–5.0 $\mu$m. The mean fine-grain particle size of primary particles of zinc oxide which constitute the above secondary aggregated particles is preferably 0.01–0.1 $\mu$m, more preferably 0.03–0.1 $\mu$m, most preferably 0.03–0.06 $\mu$m. By "secondary aggregated particles" is meant particle aggregation in which particles in conditions similar to the primary particles are flocculated with weak forces due to silicone treatment.

As to zinc oxide before silicone treatment, the zinc oxide produced by conventional methods such as the French method, U.S.A. method, wet method, etc., can be used. Among the zinc oxide produced by those production methods, the mean particle size is about 0.5 $\mu$m, the specific weight 5.4–5.6 and refractive index 1.9–2.0 in preferred cases.

The zinc oxide particles have strong surface activity and aggregate strongly. From observing this surface activity with the fading of the pigment permitted for use by law, the surface activity appears to be 5-fold of that of fine-grain titanium oxide. Furthermore, zinc oxide has strong catalytic activity and has a disadvantage in that it causes decomposition of cosmetic oil followed by a change in odor. This disadvantage can be removed by surface treatment with silicone oil, more preferably by secondary aggregation formation similar to primary particle, as surface active spots of zinc oxide can be covered. The stability of cosmetics can be increased by blending cosmetics with zinc oxide surface-treated with silicone.

In case that zinc oxide treated with silicone is blended with cosmetics, it shows good dispersibility, and the adherence and UV protection effect are improved. Furthermore, fine-grain surface-treated zinc oxide is an inorganic material and shows high stability on skin, with the expected astringency, inflammability and bactericidal effect.

The surface-treated zinc oxide which possesses such characteristics is effective in shielding UV-A region. 1 weight % has the potential of causing an increase of about 1 unit of SPF. In order to increase the SPF value only with zinc oxide, a high concentration blend is necessary, for example, although if an attempt is made to prepare an emulsion with a viscosity of 8,000–12,000 cps, cream may be obtained and the expected application form can be prepared readily.

The clay mineral applied in this invention has preferably a mean particle size of 1–25 $\mu$m (as measured by laser method) and in the alumina silicate series examples are kaolins such as kaolinite, nacrite, diccite, halocite, montmorillonites such as montmorillonite, hyderite, nontronite, saponite, illites such as cerisite hydromica, white mica, black mica, gold mica or magnesium silicate such as talc, serpentine, and chlorite.

For the present purpose, synthetic clay minerals can be employed and one or more kind of clay minerals can be used in combination. When the mean particle size of the clay minerals is smaller than 1 $\mu$m, the feel becomes very poor and fine-grain titanium oxide and zinc oxide are not effective in improving this feel. When the mean particle size is greater than 25 $\mu$m, the specific surface area becomes extremely small and fine-grain titanium oxide and zinc oxide are not effective in improving the dispensibility. Irrespective of the preparation methods of clay minerals, when the feel and the dispersibility of fine-grain titanium oxide and zinc oxide are considered platelet material as thin as possible (high aspect ratio) is preferable. The ratio (major axis of particle thickness of particle) is preferably 2–200, more preferably 5–100. The aspect ratio can be determined when the powders of clay minerals are embedded into the epoxy resin, the resulting block is cut by a diamond cutter and the sliced section of the clay minerals particle (major axis and thickness) can be observed and measured with SEM (scanning electron microscope).

The composition according to the present invention comprises fine-grain titanium oxide, zinc oxide and clay mineral each surface-treated with silicone such as dimethylpolysiloxane and methylhydrogenpolysiloxane. The relative proportions of these three components is preferably 10–80:80–10:10–30, more preferably 15–70:70–15:10–20, and much more preferably 45–65:30–10:10–20. The composition according to the present invention, especially the composition according to these specified ranges, are found to have higher protection effects than single surface-treated fine-grain titanium oxide having a high UV protection effect. It is also observed with the composition according to the present invention that the effect lasts for a long period, the optical and the catalytic activity are prevented and the lapse stability is superior.

The working mechanism is believed to be that the compositions of three kinds of powders having different mean particle size, specific weight and refractive index especially the compositions according to the above specific ranges, scatter the incident light multiply. A part of the light diminishes internally and the surface treatment agents act as a barrier to prevent micro fine-grain surface-treated titanium oxide and zinc oxide from agglomerating together, the talc which is blended in specific ratio maintains the barrier, and the dispersed states are also maintained.

When an example of the composition according to the present invention is observed with an electron scanning microscope, most of the fine-grain titanium oxide particles surface-treated do not disperse in primary particle state, but as secondary aggregates in which a few primary particles flocculate weakly, or as aggregate particles in which secondary aggregates flocculate weakly (stick partly on the surface of zinc oxide particles treated with silicone and clay mineral particles treated with silicone). Also zinc oxide particles treated with silicone in the form of secondary aggregate particles or in the form wherein secondary particles flocculate weakly and stick partly on the surface of the clay mineral particles treated with silicone. However, non-sticking particles are studded or present as their weak flocculants. The silicone-treated clay minerals used in the present invention function as supplemental dispersing agent for fine-grain titanium oxide treated with silicone and zinc oxide treated with silicone, and play a role in reaggregation prevention after elapsed time.

When the cosmetics which contain the cosmetic composition according to the present invention are prepared, particles treated with silicone which flocculate weakly in the composition according to the present invention, collapse in part to scatter in the process of the preparation. These scattered particles and weak flocculants stick o the surface of clay mineral particles treated with silicone and some of the scattered particles are studded around the clay mineral particles treated with silicone. When cosmetic layers applied on the skin are observed microscopically, scattered particles or weak flocculants of fine-grain titanium oxide treated with silicone and zinc oxide treated with silicone stick on the surface of clay mineral particles treated with silicone, and scattered particles or weak flocculants of fine-grain titanium oxide particles treated with silicone and zinc oxide particles treated with silicone which do not stick on the surface of clay mineral particles treated with silicone fill up gaps between clay mineral particles treated with silicone. In order to achieve this phenomenon, it is very important that the amount of primary particles of titanium oxide particle treated with silicone and zinc oxide particle treated with silicone is more than the amount of the primary particles which can cover completely the surface of clay mineral particles treated with silicone, and preferably the silicone-treated particles of the above three kinds are present in the above specific ratios.

Cosmetics

The amount of the composition containing the three components fine-grain titanium oxide particles treated with silicone and clay mineral particles treated with silicone is normally 0.5–50 weight % (preferably 30 weight %, more preferably 25 weight %) based o the total cosmetic weight, and more preferably 1.0–15 weight %. At less than 0.5 weight %, reduction of skin function, e.g., dryness due to sunshine and inflammation of skin, pigment settlement, etc., cannot be prevented. If over 50 weight % is used, the increase of UV protection effect is not strong relative to the blend amount, the amount used is not economical and furthermore, as a cosmetic the composition does not extend, the adherence also falls and the long term durability of UV protection effect fails. Furthermore, the formulation process, some emulsion type (viscosity 8,000–12,000 cps) cannot be easily obtained and therefore formulated forms are limited in this regard.

The present invention can be employed for all kinds of cosmetics, e.g., for foundation. Without any special restrictions, the wider area employed is, the better the results. Examples are emulsion, cream, oil foundation, emulsion foundation, etc.

In the following the present invention is explained in detail, however, it is unnecessary to say that the scope of the present invention should not be restricted in any way to the following examples. The blend proportions in the following examples are in weight parts.

EXAMPLE 1

Emulsion

| | |
|---|---|
| squalane | 14 |
| jojoba oil | 4 |
| olive oil | 2 |
| cetanol | 0.5 |
| vaseline | 1 |
| beeswax | 0.6 |
| monostearic acid sorbitan | 2.1 |
| polyoxyethylenebehenyl ether | 2.3 |
| butylparaben | 0.1 |
| 3-component composition | 10.0 | fine-graintitanium oxide treated with 5% methylhydrogen polysiloxane (mean particle size 0.9 μm).
zinc oxide treated in the same manner as above (mean particle size 2.5 μm) and talc treated in the same manner as above (mean particle size 4 μm) weight ratio of the composition = 0:40:10)

| | |
|---|---|
| 1,3-butyleneglycol | 5.0 |
| glycerol | 2.0 |
| xanthan-gum | 0.01 |
| carboxymethylcellulose sodium salt | 0.14 |
| perfume | 0.1 |
| purified water | 56.15 |

EXAMPLE 2

Cream

| | |
|---|---|
| behenic acid | 1.0 |
| cetanol | 0.5 |
| cholesterol | 1.0 |
| olive oil | 1.0 |
| beeswax | 2.0 |
| myristic acid actyldodecyl | 5.0 |
| squalane | 11.0 |
| vaseline | 1.0 |

-continued

| | |
|---|---|
| monostearic acid sorbitan | 1.6 |
| butylparaben | 0.1 |
| purified lanolin | 3.5 |
| monostearic acid polyethylene glycol | 1.8 |
| 3-component composition | 10.0 | fine grain titanium oxide treated with 10% dimethylpolysiloxane (mean particle size 1.2 μm), zinc oxide treated in the same manner as above (mean particle size 1.8 μm) and talc treated in the same manner as above (mean particle size 6 μm) (weight ratio of the composition = 30:50:20)

| | |
|---|---|
| propyleneglycol | 2.0 |
| 1,3-butyleneglycol | 3.0 |
| triethanolamine | 0.3 |
| methylparaben | 0.2 |
| purified water | 55.0 |

EXAMPLE 3

Cosmetic Water

| | |
|---|---|
| purfied water | 88.0 |
| propyleneglycol | 1.0 |
| polyoxyethylene hardened caster oil | 0.4 |
| ethanol | 8.0 |
| 4-component composition | 10.0 | fine-grain titanium oxide treated with 3% dimethylpolysiloxane (mean particle size 0.5 μm), zinc oxide treated in the same manner as above (mean particle size 3.0 μm), talc treated in the same manner as above (mean particle size 3 μm) and kaolin treated in the same manner as above (mean particle size 5 μm) (weight ratio of the composition = 40:30:15:15)

| | |
|---|---|
| allantoin | 0.05 |
| citric acid | 0.02 |
| sodium hydrogen phosphate | 0.13 |
| sorbitol | 0.2 |
| L-serine | 0.2 |
| EDTA2Na | 0.1 |

EXAMPLE 4

Oily Foundation

| | |
|---|---|
| squalane | 56.8 |
| cetyloctanate | 5.0 |
| microcrystalline wax | 6.0 |
| talc | 10.0 |
| 3-component composition | 10.0 | fine-grain titanium oxide treated with 15% dimethylpolysiloxane (mean particle size 2.0 μm), zinc oxide treated in the same manner as above (mean particle size 4.5 μm) and mica treated in the same manner as above (mean particle size 10 μm) (weight ratio of the composition = 30:50:20)

| | |
|---|---|
| coloring pigment | 12.0 |
| perfume | 0.2 |

EXAMPLE 5

Emulsified Foundation

| | |
|---|---|
| stearic acid | 1.75 |
| cetyloctanate | 3.0 |
| monostearic acidpolyethylene glycol | 2.0 |
| monostearic acid glycerol | 3.0 |
| color paste | 15.0 |
| 3-component composition | 10.0 | fine-grain titanium oxide treated with 2% methylhydrogen polysiloxane (mean particle size 0.7 μm), zinc oxide treated in the same manner as -continued

| | |
|---|---|
| above (mean particle size 1.0 μm) and talc treated in the same manner as above (mean particle size 5 μm) (weight ratio of the composition = 10:80:10) | |
| butylparaben | 0.1 |
| P.E.G. (polyethylene glycol) | 6.0 |
| carboxymethylcellulose sodium salt | 0.1 |
| methylparaben | 0.2 |
| triethanolamine | 0.7 |
| aluminum magnesium silicate | 1.0 |
| purified water | 57.15 |

EXAMPLE 6

Powder Foundation

| | |
|---|---|
| talc treated by amino acid | 61.3 |
| Sericite treated with fluorine | 8.0 |
| titanium oxide treated with lecithin | 15.0 |
| nylon powder | 2.4 |
| 3-component composition | 9.6 |
| fine-grain titanium oxide treated by 20% dimethylpolysiloxane (mean particle size 3.0 μm), zinc oxide treated in the same manner as above (mean particle size 5.0 μm) (and sericite treated in the same manner as above (mean particle size 7 μm) (weight ratio of the composition = 80:10:10) | |
| red iron oxide | 1.0 |
| hydrated iron oxide | 2.1 |
| ultramarine blue pigment | 0.4 |
| perfume | 0.2 |

EXAMPLE 7

Powder Foundation

| | |
|---|---|
| talc | 7.5 |
| sericite | 20.0 |
| mica powder | 12.5 |
| titanium oxide | 2.0 |
| 3-component composition | 40.0 |
| fine-grain titanium oxide treated with 10% dimethylpolysiloxane, zinc oxide treated in the same manner as above and mica treated in the same manner as above (weight ratio of the composition = 50:35:15) | |
| iron oxide yellow | 3.5 |
| iron oxide black | 0.5 |
| iron oxide red | 2.0 |
| liquid paraffin | 5.0 |
| stearyl alcohol | 3.0 |
| beeswax | 3.0 |
| squalane | 1.0 |

Examples for preparation of fine-grain titanium oxide treated with silicone and fine-grain zinc oxide treated with silicone are shown below.

PREPARATION EXAMPLE 1

Titanium oxide (Ishihara Industry Co. TTO-51A), zinc oxide (Sakai Chemistry fine-grain zinc white) and sericite (Sansin Kougyou Co. FSE) are mixed in a ratio 50:30:20 (weight ratio) and the mixture (5 kg) and polymethyltrimethoxysiloxane (250 g) are mixed in a Henschel mixer and pulverized with a fluidized jet mill 100 AFG (Alpine Co.) under nozzle air pressure of 4 kg/cm$^2$. The final composition of fine grain titanium oxide, zinc oxide and sericite(5:3:2 weight ratio) each treated with 5% dimethylpolysiloxane was obtained.

PREPARATIVE EXAMPLE 2

Titanium oxide (Nihon Aerojil Co. p-25) (10 kg) and dimethylpolysiloxy silanol (1 kg) are mixed in a Henschel mixer and pulverized with the above jet mill under 5 kg/cm$^2$ air pressure to obtain fine-grain titanium oxide treated with 10% dimethylpolysiloxane. Zinc oxide (Sumitomo Cement Co. ZnO-350) (10 kg) and polymethyl-triethoxysiloxane (500 g) are mixed in a Henschel mixer and pulverized with the above jet mill under air pressure 6 kg/cm$^2$ to obtain fine-grain zinc oxide treated with 5% dimethylpolysiloxane. Talc (Asada Mill Co., talc JA-46R) (5 kg) and dimethylpolysiloxane (100 g) are mixed in a Henschel mixer and pulverized with the above jet mill under pressure of 6.5 kg/cm$^2$ to obtain talc treated with 2% dimethylpolysiloxane. The obtained fine-grain titanium oxide (5.5 kg) treated with 10% dimethyl-polysiloxane, fine-grain zinc oxide treated with 5% diemthylpoly-siloxane (3 kg) and 2% dimethylpolysiloxane (1 kg) are mixed in a high speed Henschel mixer to obtain the composition of fine-grain titanium oxide, fine-grain zinc oxide and talc (555:30:10 weight ratio) each treated with 7.2% dimethylpolysiloxane.

Utilizing the above Examples 1 and 2 and changing the composition ratio of the above fine-grain titanium oxide treated with silicone, the above zinc oxide treated with silicone and the above talc treated with silicone. SPF and PFA values with in-vitro methods are determined. Also SPF and PFA values of reference samples containing only one or two of the three kinds of particles treated with silicone are determined. The blend ratio of the composition in cosmetics is 10 weight part. The SPF and PFA values of Comparative Examples which, except for silicone treatment, are identical to Examples 1 and 2, are determined. The SPF and PFA values thus obtained are summarized in Table 1.

TABLE 1

| Composition ratio TiO$_2$:ZnO:talc | Example 1 with surface treatment | | Comparison 1 without surface treatment | | Example 2 with surface treatment | | Comparison 2 without surface treatment | |
|---|---|---|---|---|---|---|---|---|
| | SPF values | PFA values | SPF values | PFA values | SPF values | PFA values | SPF values | PFA values |
| *100:0:0 | 32.6 | 26.1 | 27.5 | 22.0 | 31.9 | 25.6 | 26.8 | 21.0 |
| *90:10:0 | 33.0 | 26.8 | 29.0 | 23.1 | 32.8 | 27.9 | 28.3 | 22.5 |
| 80:10:0 | 42.5 | 35.3 | 37.4 | 30.0 | 41.6 | 35.7 | 35.4 | 28.1 |
| 70:20:10 | 43.9 | 37.3 | 37.7 | 30.2 | 44.0 | 37.8 | 37.5 | 30.0 |

TABLE 1-continued

| Composition ratio TiO$_2$:ZnO:talc | Example 1 with surface treatment SPF values | Example 1 with surface treatment PFA values | Comparison 1 without surface treatment SPF values | Comparison 1 without surface treatment PFA values | Example 2 with surface treatment SPF values | Example 2 with surface treatment PFA values | Comparison 2 without surface treatment SPF values | Comparison 2 without surface treatment PFA values |
|---|---|---|---|---|---|---|---|---|
| 60:30:10 | 47.2 | 40.1 | 39.0 | 30.8 | 48.5 | 41.0 | 39.2 | 30.5 |
| 50:40:10 | 45.6 | 39.2 | 38.2 | 30.1 | 47.3 | 40.2 | 39.0 | 31.0 |
| 40:50:10 | 45.1 | 39.0 | 37.0 | 29.2 | 46.1 | 39.7 | 38.1 | 30.5 |
| 30:60:10 | 44.7 | 38.2 | 38.1 | 30.0 | 41.5 | 35.3 | 37.5 | 30.0 |
| 20:70:10 | 41.2 | 35.0 | 38.2 | 29.9 | 40.9 | 35.1 | 36.9 | 29.3 |
| 10:80:10 | 40.3 | 34.1 | 38.1 | 29.4 | 40.0 | 33.2 | 33.1 | 26.5 |
| *10:90:0 | 15.5 | 12.9 | 13.4 | 10.1 | 20.3 | 17.5 | 16.7 | 13.9 |
| *0:100:0 | 10.8 | 9.0 | 7.9 | 7.0 | 10.1 | 9.3 | 7.5 | 6.9 |
| *80:0:20 | 25.3 | 21.4 | 20.2 | 15.9 | 26.1 | 22.0 | 19.5 | 15.1 |
| 70:10:20 | 35.5 | 30.6 | 30.1 | 24.1 | 36.1 | 30.9 | 30.4 | 24.3 |
| 60:20:20 | 39.3 | 33.6 | 31.2 | 24.8 | 40.2 | 34.5 | 30.0 | 23.1 |
| 50:30:20 | 40.6 | 34.5 | 30.7 | 24.3 | 41.6 | 35.0 | 29.3 | 23.0 |
| 40:40:20 | 45.2 | 39.0 | 31.5 | 25.6 | 48.5 | 39.2 | 29.5 | 22.4 |
| 30:50:20 | 43.3 | 36.9 | 30.5 | 23.6 | 42.9 | 37.1 | 30.4 | 23.5 |
| 20:60:20 | 38.0 | 32.1 | 27.6 | 22.9 | 39.2 | 33.0 | 26.3 | 21.0 |
| *0:80:20 | 15.7 | 12.7 | 13.3 | 10.7 | 16.3 | 13.9 | 12.3 | 9.5 |
| *70:0:30 | 21.4 | 17.0 | 17.0 | 12.8 | 20.7 | 16.0 | 15.5 | 12.0 |
| 60:10:0 | 32.2 | 27.0 | 22.1 | 17.5 | 31.9 | 27.0 | 24.2 | 18.0 |
| 50:20:30 | 39.0 | 33.3 | 24.2 | 19.0 | 38.9 | 33.1 | 28.0 | 22.3 |
| 40:30:30 | 40.5 | 34.0 | 25.0 | 20.0 | 41.3 | 35.9 | 29.6 | 23.7 |
| 30:40:30 | 41.6 | 35.1 | 20.1 | 16.0 | 41.0 | 35.0 | 24.3 | 19.0 |
| 20:50:30 | 35.9 | 30.6 | 20.5 | 16.2 | 40.5 | 34.5 | 21.5 | 17.0 |
| 10:60:30 | 35.0 | 30.2 | 19.0 | 15.0 | 34.2 | 28.0 | 19.7 | 15.0 |
| *0:70:30 | 14.0 | 11.1 | 12.2 | 9.8 | 15.0 | 13.1 | 10.3 | 8.5 |

Remarks: * denotes reference sample with surface treatment.

For the examples for which SPF and PFA values are determined (Examples 1–2, Reference Sample and Comparative Examples 1, 2) the SPF and PFA values are determined one year later with in-vitro methods The results obtained are summarized in Table 2.

TABLE 2

| Composition ratio TiO$_2$:ZnO:talc | Example 1 with surface treatment SPF values | Example 1 with surface treatment PFA values | Comparison 1 without surface treatment SPF values | Comparison 1 without surface treatment PFA values | Example 2 with surface treatment SPF values | Example 2 with surface treatment PFA values | Comparison 2 without surface treatment SPF values | Comparison 2 without surface treatment PFA values |
|---|---|---|---|---|---|---|---|---|
| *100:0:0 | 32.6 | 26.0 | 27.0 | 21.2 | 31.8 | 25.4 | 24.1 | 18.3 |
| **90:10:0 | 33.0 | 26.8 | 28.0 | 22.5 | 32.6 | 27.8 | 25.5 | 21.4 |
| 80:10:10 | 42.6 | 35.3 | 30.0 | 23.0 | 41.5 | 35.7 | 23.4 | 17.5 |
| 70:20:10 | 43.6 | 37.1 | 30.6 | 24.1 | 44.3 | 37.9 | 22.2 | 17.0 |
| 60:30:10 | 47.5 | 40.2 | 31.2 | 23.9 | 48.3 | 40.9 | 25.3 | 20.2 |
| 50:40:10 | 45.6 | 39.2 | 29.4 | 23.2 | 47.0 | 40.1 | 20.4 | 16.1 |
| 40:50:10 | 45.1 | 39.0 | 28.3 | 22.2 | 46.1 | 39.7 | 21.2 | 16.5 |
| 30:60:10 | 44.3 | 38.0 | 25.5 | 20.0 | 41.4 | 35.3 | 21.7 | 17.2 |
| 20:70:10 | 42.5 | 35.4 | 23.7 | 18.0 | 40.9 | 35.1 | 20.0 | 15.5 |
| 10:80:10 | 40.0 | 34.0 | 25.5 | 19.5 | 40.0 | 33.2 | 18.1 | 13.2 |
| *10:90:0 | 14.0 | 11.6 | 10.2 | 7.8 | 18.8 | 14.2 | 10.5 | 7.2 |
| *0:100:0 | 10.0 | 8.2 | 4.5 | 3.2 | 9.1 | 7.0 | 5.0 | 3.7 |
| *80:0:20 | 24.9 | 21.2 | 10.5 | 8.0 | 25.0 | 21.1 | 18.1 | 14.5 |
| 70:10:20 | 35.4 | 30.5 | 12.3 | 9.7 | 36.0 | 30.8 | 13.3 | 10.3 |
| 60:20:20 | 39.3 | 33.6 | 11.4 | 9.0 | 40.1 | 34.4 | 14.2 | 11.4 |
| 50:30:20 | 40.4 | 34.3 | 15.2 | 12.0 | 41.6 | 35.0 | 13.1 | 10.7 |
| 40:40:20 | 45.1 | 39.0 | 13.2 | 10.2 | 46.4 | 39.2 | 12.6 | 10.0 |
| 30:50:20 | 43.3 | 36.9 | 12.7 | 10.1 | 42.9 | 37.1 | 11.5 | 9.0 |
| 20:60:20 | 38.0 | 32.1 | 11.8 | 9.0 | 39.2 | 33.0 | 10.3 | 7.5 |
| *0:80:20 | 12.3 | 9.8 | 7.0 | 5.3 | 15.0 | 12.6 | 7.4 | 5.9 |
| *70:0:30 | 15.1 | 12.3 | 10.1 | 7.5 | 18.3 | 15.2 | 12.7 | 10.0 |
| 60:10:30 | 31.1 | 26.7 | 11.4 | 9.0 | 31.5 | 26.8 | 12.4 | 9.7 |
| 50:20:30 | 38.9 | 33.1 | 11.0 | 8.8 | 38.5 | 33.0 | 12.9 | 9.8 |
| 40:30:30 | 40.4 | 34.0 | 10.3 | 7.6 | 41.0 | 35.8 | 10.3 | 7.5 |
| 30:40:30 | 41.6 | 35.1 | 11.5 | 9.1 | 41.0 | 35.0 | 10.0 | 8.0 |
| 20:50:30 | 35.8 | 30.5 | 12.0 | 9.6 | 40.0 | 34.3 | 9.5 | 7.1 |
| 10:60:30 | 34.9 | 30.1 | 9.9 | 7.4 | 34.0 | 27.9 | 9.7 | 7.2 |
| *0:70:30 | 10.4 | 8.1 | 6.5 | 5.0 | 10.3 | 8.0 | 5.0 | 4.1 |

Remarks: * denotes reference sample with surface treatment

As seen above, the SPF and PFA values differ widely with the presence and absence of surface treatment and according to the composition ratio and the compositions and cosmetics according to the present invention are found to have high UV protection effect.

(1) Test of optical and catalytic activity

Compositions 18 g containing fine graintitanium oxide treated with 5% dimethylpolysiloxane, zinc oxide treated similarly and talc treated similarly (weight ratio 40:50:10) are mixed with Yellow 401 (2g) or Red 202 (2 g) in a Raikai mixer for 15 minutes and the resulting mixture is irradiated with a UV lamp (560 $\mu$m/cm$^2$ for 20 days. Compositions (18 g) containing fine-grain titanium oxide, zinc oxide and talc without the siliconization (weight ratio 40:50:10) are tested similarly. The results are summarized in Table 3.

TABLE 3

| pigment | surface treatment | | measured values (L. ab) | | |
|---|---|---|---|---|---|
| Y-401 | no treatment (sample for comparison) | before irradiation | 66.73 | 0.73 | 66.30 |
| | | after irradiation | 50.91 | 0.66 | 42.57 |
| | compositions of fine-grain titanium oxide, zinc oxide and talc each treated with 5% dimethylpolysiloxane (50:40:10) | before irradiation | 67.43 | 0.92 | 68.59 |
| | | after irradiation | 67.20 | 0.91 | 68.57 |
| R-202 | no treatment (sample for comparison) | before irradiation | 36.23 | 35.23 | 18.44 |
| | | after irradiation | 41.66 | 27.40 | 2.21 |
| | compositions of fine-grain titanium oxide, zinc oxide and talc each treated with 3% dimethylpolysiloxane (50:40:10) | before irradiation | 34.16 | 34.21 | 19.74 |
| | | after irradiation | 34.02 | 34.30 | 19.52 |

The colors of test samples containing Y-401 (Yellow 401) and R-202 (Red 202) without silconization are faded remarkably, however fading of test samples containing fine-grain titanium oxide, zinc oxide and talc surface-treated with silicone is prevented remarkably.

Test of heat catalytic activity 10 g of each oil (silicone (Shin-etsu Chemical Co. KF 96 (50 cs)), squalane and octyldodecyl oleate) and 0.1 g of test sample are placed in small glass bottles having a capacity of 20 cc and are dispersed with ultrasonic wave for 15 minutes. These dispersed samples are allowed to stand in thermostats at 90° C. and 150° C. When fading or discoloring of these samples is observe, the tests are terminated and employing FT-IR (Fourier transform IR spectrometer), the oxidation of the oils(structure change) is measured with the peroxide measurements. The results are shown in Table 4.

TABLE 4

<P.O.V. values measured>

| type of surface treatment | sorts of oils | 90° C./5 h | 150° C./2 h |
|---|---|---|---|
| no treatment (sample for comparison) | squalane | or less 0.1 | 10.5 |
| | octyldodecyl oleate | 7.0 | 11.4 |
| compositions of fine-grain titanium oxide, zinc oxide and talc each treated with 3% | squalane | or less 0.1 | 6.0 |

TABLE 4-continued

<P.O.V. values measured>

| type of surface treatment | sorts of oils | 90° C./5 h | 150° C./2 h |
|---|---|---|---|
| dimethylpolysiloxane (40:30:30) | octyldodecyl oleate | 7.2 | 8.9 |
| blank | squalane | or less 0.1 | 12.0 |
| | octyldodecyl oleate | 9.0 | 10.1 |

The compositions surface-treated with silicone are tested under accelerated test at 150° C. for 2 hours. It is found that the P.O.V. (peroxide values) are lower and the oils retain more stability than in samples without silicone treatment and in blank samples. The color changes of fine-grain oxide with the accelerated tests are observed. The test samples with silicone treatment retain a white color, but those without silicone treatment become brown.

Due to the accelerated tests (150° C., 2 hours), test samples with surface treatment and blank samples show similar values, indicating no structural changes. In contrast with these results, the test samples without treatment have a lower ratio of peak height, indicating structural changes. The peak height ratios of optical absorptions of atomic groups measured with TF-IR are shown in Table 5.

TABLE 5

(peak hight ratio of optical absorption by atomic group measured with FT-IR>

| 1. in case of KF96 (50 cs), peak hight ratio 1256 cm$^{-1}$ (Si—CH$_2$)/ 2962 cm$^{-1}$ (—CH$_2$) | | |
|---|---|---|
| state for oils | 90° C./5 h | 150° C./2 h |
| blank | 2.564 | 2.593 |
| no treatment (sample for comparison) | 2.498 | 1.809 |
| compositions of fine grain titanium oxide, zinc oxide and talc each treated with 3% dimethylpoiysiloxane (40:50:10) | 2.558 | 2.603 |
| 2. in case of squalane, peak hight ratio 2954 cm$^{-1}$ (—CH$_3$)/ 1464 cm$^{-1}$ (=CH$_2$) | | |
| state for oils | 90° C./5 h | 150° C./2 h |
| blank | 3.067 | 3.060 |
| no treatment (sample for comparison) | 2.937 | 2.604 |
| compositions of fine-grain titanium oxide, zinc oxide and talc each treated with 3% dimethylpoiysiloxane (40:50:10) | 3.071 | 3.051 |
| 3. in case of octyldodecyloleate peak hight ratio 2954 cm$^{-1}$ (—CH$_2$)/ 1740 cm$^{-1}$ (=(C=O) | | |
| state of oils | 90° C./5 h | 150° C./2 h |
| blank | 2.295 | 2.263 |
| no treatment (sample for comparison) | 1.882 | 1.263 |
| compositions of fine-grain titanium oxide, zinc oxide and talc each treated with 3% dimethylpolysilioxane (40:50:10) | 2.288 | 2.240 |

As evident from the above results, cosmetics according to the present invention have good dispersibility and high UV protection effect, prevent optical and catalytic activity and exhibit no change with the lapse of time and high stability.

The sunburn index SPF and PFA values can be measured with a SPF analyzer (Optometrics Co. SPF-290 analyzer) according to the following procedures.

Procedure 1

1. On a quarter plate with length of 100 mm, width of 100 mm and thickness of 3 mm a transporesurgical tape (3M Co.) is affixed and on this tape an area 6.4 cm×6.4 cm (40 cm$^2$) for sample application is kept.

2. On the above area for application, 0.05 g of sample (1.25 mg/cm$^2$) is applied with a sponge puff.

3. The 9 irradiation spots with 16 mm diameter in the application area are settled and measured with the above SPF analyzer and SPF and PFA values are derived from the mean values of 9 measurements.

4. For some samples the above measurements are repeated a few times and the mean values are determined from the measured values.

Procedure 2

Liquid foundation or cream

1. On a quartz plate with length of 100 mm, width of 100 mm and thickness of 3 mm a transporesurgical tape (3M Co.) is affixed and on this tape an area 6.4 cm×6.4 cm (40 cm$^2$) for sample application is kept.

2. On the above area for application, 0.08 g of sample (2.0 mg/cm$^2$) is applied with a sponge puff and allowed to stand for 15 minutes.

3. The 9 irradiation spots with 16 mm diameter in the application area are settled and measured with the above SPF analyzer and SPF and PFA values are derived from the mean values of 9 measurements.

4. For some samples the above measurements are repeated a few times and the mean values are determined from the measured values.

In the following it is shown that a silicone treatment methods for fine-grain titanium oxide and fine-grain zinc oxide, usage of the jet method described in the JP Patent Kokoku publication JP-B 6-59397 gives favorable results.

The dispersibility, SPF values and degree of hydrophocity of fine-grain titanium oxide treated with silicone and fine-grain zinc oxide treated with silicone obtained by the methods which are described in the JP Patent Kokai publication JP-A-62-228006 and fine-grain titanium oxide treated with silicone and fine-grain zinc oxide treated with silicone obtained by the jet method which are described in the JP Patent Kokoku Publication JP-B-6-59397 are evaluated.

In the methods described in the JP Patent Kokai publication JP-A-2-228006 titanium oxide(or zinc oxide)and silicone oil dissolved in a solvent are mixed in a slow blender under sufficient heating and afterwards the solvent is distilled and the residue is heated 90–405° C. Fine-grain titanium oxide treated with silicone and fine-grain zinc oxide treated with silicone obtained with the method described in the JP Patent Kokoku JP-B-6-59397 (obtainable with methods similar to those in the Production Example 2) are used.
Evaluation item and evaluation method dispersibility 5 g of each of the fine-grain titanium oxide treated as above and fine-grain zinc oxide treated as above are precisely weighed and mixed with liquid paraffin under 300 r.p.m. with stirring for 5 minutes and a paste is formed. The particle size in the aggregates are measured with a particle gauge instrument (Hegman gauge: measurement range 0–25 m). (3 measurements)

SPF values

The paste used for the above measurement of dispersibility is used also for measurement similar to the above procedure 2 with an in-vitro method. SPF analyzer (Optometrics Co. SPF-290 Analyzer) (5 measurements).

Hydrophobicity

Purified water (10 ml) is weighed in a test tube (20 ml) and 0.1 g of powders treated with silicone in (1) and (2) are weighed. After manual shaking 100 times, it is allowed to stand for one day at room temperature and afterwards shaken again 100 times. On the next day, the conditions of powders treated with silicone which gather near the water-air interface are evaluated.

⊚: Powders treated with silicone gather completely near the water-air interface and the dispersion medium "water" is completely transparent.

○: Powders treated with silicone gather completely near the water-air interface, but the dispersion medium "water" is semitransparent and the particles are dispersed and a part of them settled on the bottom of the test tube.

Measured according to the method described in JP Patent Kokai publication JP-A-62-228006, the dispersibility is 20 $\mu$m, the SPF value 14.8 and the hydrophobicity is rated ○. In contrast to this according to the above jet method, the dispersibility is 5 $\mu$m, the SPF value 21.2 and the hydrophobicity is rated ⊚.

As seen from the foregoing results, the size of the aggregated block measured with a particle gauge is reduced to one fourth in the case of production with the jet method compared to the old method. Furthermore, the SPF values are obviously superior in the case of jet method and the hydrophobicity is also superior.

The cosmetics compositions according to the invention which contain fine-grain titanium oxide treated with silicone, zinc oxide treated with silicone and clay mineral treated with silicone exhibit the following fundamental effects:

1. They possess excellent UV protection effects and moreover the effect can be retained for a long period.

2. When the cosmetics containing fine-grain titanium oxide treated with silicone, zinc oxide treated with silicone and clay mineral treated with silicone are used, they very seldom cause change in other components in the cosmetics because they suppress the optical activity and catalytic activity. For instance, it is possible to prevent odor development and denaturating of oils for cosmetics and discoloring and fading of tar pigment permitted for use by laws.

3. Fine-grain titanium oxide treated with silicone, zinc oxide treated with silicone and clay mineral treated with silicone are superior in dispersibility in the cosmetics and can prevent reaggregation, because they are similarly treated with silicone and their surface properties are similar.

The cosmetic compositions according to the invention which contain specific ratios of fine-grain titanium oxide treated with silicone, zinc oxide treated with silicone and clay mineral treated with silicone display the above fundamental effects in a remarkable manner.

In the cosmetic compositions according to the invention in which one or more kind of fine-grain titanium oxide treated with silicone, zinc oxide treated with silicone and clay mineral treated with silicone aggregate secondarily, the above fundamental effects are remarkable.

In the cosmetic compositions according to the invention in which the secondarily aggregated particles have specific mean particle size, the above fundamental effects are more remarkable. In the cosmetic compositions according to the invention wherein one or more of fine-grain titanium oxide treated with silicone, zinc oxide treated with silicone and clay mineral treated with silicone is prepared by pulverization with a jet stream, simultaneously adsorbing or combining silicone thereto, the above fundamental effects are more remarkable.

The cosmetics according to the invention which contain cosmetic composition according to the invention exhibit the following fundamental effects:

1. They exhibit excellent UV protection effects which are retained over the long term.

2. When cosmetics which contain fine-grain titanium oxide treated with silicone, zinc oxide with silicone and clay mineral treated with silicone are used, they very seldom cause changes in other compositions in the cosmetics, because they suppress the optical and catalytic activity. For instance, it is possible to prevent odor development and denaturating of oils for cosmetics and discoloring and fading of tar pigment permitted for use by laws.

3. Fine-grain titanium oxide treated with silicone zinc oxide treated with silicone and clay mineral treated with silicone are superior in dispersibility in the cosmetics and can prevent reaggregation, because they are similarly treated with silicone and their surface properties are similar. In the cosmetics according to the invention which contains a specific amount of the cosmetic composition relative to total amount of the cosmetic, the effects of cosmetics according to the present invention are remarkable.

We claim:

1. A cosmetic composition comprising:
   10–80 parts by weight of fine-grain titanium oxide treated with silicone;
   (b) 80–10 parts by weight of zinc oxide treated with silicone; and
   (c) 10–30 parts by weight of clay mineral treated with silicone.

2. The cosmetic composition of claim 1, comprising:
   (a) 15–70 parts by weight of fine-grain titanium oxide treated with silicone;
   (b) 70–15 parts by weight of zinc oxide treated with silicone; and
   (c) 10–20 parts by weight of clay mineral treated with silicone.

3. The cosmetic composition of claim 1, comprising:
   (a) 45–65 parts by weight of fine-grain titanium oxide treated with silicone;
   (b) 30–10 parts by weight of zinc oxide treated with silicone; and
   (c) 10–20 parts by weight of clay mineral treated with silicone.

4. The cosmetic composition of any one of claims 1–3, wherein one or more of said fine-grain titanium oxide treated with silicone, said zinc oxide treated with silicone, and said clay mineral treated with silicone aggregate secondarily.

5. The cosmetic composition of claim 4, wherein the mean particle size of said fine-grain titanium oxide as secondarily aggregated is 0.5–3.0 µm; the mean particle size of said zinc oxide as secondarily aggregated is 0.01–5.0 µm, and the mean particle size of said mineral clay as secondarily aggregated is 1–25 µm.

6. The cosmetic composition of any one of claim 1–3, wherein one or more of said fine-grain titanium oxide treated with silicone, said zinc oxide treated with silicone, and said clay mineral treated with silicone are prepared by pulverizing and/or grinding one or more titanium oxide, zinc oxide and clay mineral, and simultaneously adsorbing and binding silicone thereto.

7. The cosmetic composition of claim 4, wherein one or more of said fine-grain titanium oxide treated with silicone, said zinc oxide treated with silicone, and said clay mineral treated with silicone are prepared by pulverizing and/or grinding one or more titanium oxide, zinc oxide and clay mineral, and simultaneously adsorbing and binding silicone thereto.

8. The cosmetic composition of claim 5, wherein one or more of said fine-grain titanium oxide treated with silicone, said zinc oxide treated with silicone, and said clay mineral treated with silicone are prepared by pulverizing and/or grinding one or more titanium oxide, zinc oxide and clay mineral, and simultaneously adsorbing and binding silicone thereto.

9. A cosmetic comprising the cosmetic composition according to any one of claims 1–3.

10. A cosmetic comprising the cosmetic composition according to claim 4.

11. The cosmetic of claim 9, wherein said composition is present in the cosmetic in an amount of 0.5–50 weight % based on the total weight of the cosmetic.

12. The cosmetic of claim 10, wherein said composition is present in the cosmetic in an amount of 0.5–50 weight % based on the total weight of the cosmetic.

13. The cosmetic of claim 9, wherein said composition is present in the cosmetic in an amount of 5–20 weight % based on the total weight of the cosmetic.

14. The cosmetic of claim 10, wherein said composition is present in the cosmetic in an amount of 5–20 weight % based on the total weight of the cosmetic.

* * * * *